United States Patent [19]

Carver et al.

[11] Patent Number: 5,549,830

[45] Date of Patent: Aug. 27, 1996

[54] REVERSE OSMOSIS AND ULTRAFILTRATION METHODS FOR SOLUTIONS TO ISOLATE DESIRED SOLUTES INCLUDING TAXANE

[75] Inventors: David R. Carver; Timothy R. Prout; Christopher T. Workman; Charles L. Hughes, all of Boulder, Colo.

[73] Assignee: NaPro BioTherapeutics, Inc., Boulder, Colo.

[21] Appl. No.: 203,653

[22] Filed: Feb. 28, 1994

Related U.S. Application Data

[63] Continuation of Ser. No. 982,482, Nov. 27, 1992, abandoned.

[51] Int. Cl.$^6$ ..................................................... B01D 61/14
[52] U.S. Cl. ............................................ 210/641; 210/651
[58] Field of Search ................................. 210/641, 651, 210/652, 650; 426/590; 435/41

[56] References Cited

U.S. PATENT DOCUMENTS

| | | | |
|---|---|---|---|
| 3,883,425 | 5/1975 | Dorn | 210/650 X |
| 4,966,892 | 10/1990 | McAnalley | 426/590 X |
| 5,019,504 | 5/1991 | Christen et al. | 435/41 X |
| 5,084,182 | 1/1992 | Arthur | 210/642 |
| 5,098,575 | 3/1992 | Yaeli | 210/652 |
| 5,102,539 | 4/1992 | Siegfried | 210/490 X |
| 5,106,734 | 4/1992 | Nielsen | 435/84 |
| 5,108,604 | 4/1992 | Robbins | 210/321.74 |
| 5,108,879 | 4/1992 | Abe et al. | 430/429 |
| 5,330,756 | 7/1994 | Steuart et al. | 424/405 |

OTHER PUBLICATIONS

*Standard Methods for the Examination of Water and Wastewater,* 17th Edition, pp. 1–56.
Membrane Products, Selective Reverse Osmosis Membranes (Advertisement).

*Primary Examiner*—Frank Spear
*Attorney, Agent, or Firm*—Timothy J. Martin

[57] ABSTRACT

A method of processing a feed liquid in the form of an extraction solution containing taxane solutes that is an extraction product of a biomass utilizes at least one semipermeable membrane to remove at least one taxane solute from the solvent by reverse osmosis. The feed liquid is placed in a first region on one side of the membrane and pressure is supplied to transport constitutes of the feed liquid across the membrane to a second region as a first permeate while retaining a first retentate in the first region. The taxane solute may be either retained or transported. Where the taxane solute is transported, the method can further include the use of a second semipermeable membrane of a pore size different from the first membrane and supplying a pressure to transport some of the first permeate across the second membrane as a second permeate while retaining a majority of the desired taxane solute as a second retentate. Here, the first membrane has a pore size which allows transport of the taxane solute while the second membrane has a pore size that retains the taxane solute. A variety of solvents and useable membranes is disclosed.

24 Claims, 1 Drawing Sheet

REVERSE OSMOSIS AND ULTRAFILTRATION METHODS FOR SOLUTIONS TO ISOLATE DESIRED SOLUTES INCLUDING TAXANE

This is a continuation of application Ser. No. 07/982,482 filed on Nov. 27, 1992, now abandoned.

FIELD OF THE INVENTION

Generally, the present invention relates to a method for processing a feed liquid in order to remove a solute dissolved or suspended therein. Specifically, the present invention relates to a method of processing an aqueous feed liquid containing a mixture of solutes in order to remove a desired solute. More specifically, this method is directed to the concentration and purification of taxane material present in a solution, and this method is described below with respect to the taxane concentration and purification application in order to produce a taxane product.

BACKGROUND

The method of the present invention utilizes a reverse osmosis technique or an ultrafiltration technique to concentrate/purify the quantity of solutes in a feed liquid. The classification of a process as either reverse osmosis or ultrafiltration depends on pore size of the membrane. Reverse osmosis membranes have a nominal molecular weight cutoff of less than or equal to 1000 daltons; ultrafiltration membranes have nominal molecular weight cutoff of greater than 1000 daltons. The selection of the membrane pore size for any specific application is based on the size of the solute which must be removed. Once the membrane is selected, a feed liquid is contacted with one side of a semipermeable membrane under pressure. The solvent and the smaller solutes in the feed liquid are then forced through the pores of the semipermeable membrane while the other solutes are rejected because of their inability to be transported through these pores due to the size of these solutes.

The present invention utilizes a reverse osmosis process to concentrate/purify a solute in a nonaqueous solution containing a mixture of solutes. A nonaqueous solution is defined as a solution that does not contain water as its major solvent constituent. Reverse osmosis membranes are typically manufactured so that the membranes are permeable to aqueous solutions. A membrane that is adapted to pass $H_2O$ can show substantially different characteristics with nonaqueous solvents. Thus, reverse osmosis is commonly used with aqueous solutions, for example, to desalinate saline water, to concentrate fruit juices, to purify waste water and to remove water from milk.

The use of nonaqueous solutions in a ultrafiltration process is a common laboratory procedure. However, ultrafiltration membranes have not been employed to purify and concentrate taxane materials.

In the present invention, reverse osmosis and ultrafiltration are used to purify/concentrate taxanes. Taxanes are a group of diterpenes found in certain types of natural vegetation such as the Western Yew, (*Taxus brevifolia*). Examples of taxanes are taxol, cephalomannine, baccatin III and the like. Taxanes, specifically taxol, have become the subject of extensive research in the medical world because taxol evidences anticancer activity. Many other taxanes do not evidence this anticancer activity; however, these other taxanes are of interest because they can be synthesized in the laboratory into taxol or taxol like compounds.

The most readily available and accessible means of generating taxol is to extract it and other taxanes from plant material. There is a low taxol and taxane concentration in the biomass (i.e., the plant material) making extraction of the desired material difficult. Large quantities of solvent are required to extract the desired taxanes from the biomass. The solution resulting from this extraction process is the miscelle. Typically, the miscelle contains a minute concentrate of taxanes and a large amount of solvent and solid residue.

To facilitate isolation of the taxane material or further purification/concentration, these taxane solutions have a large portion of the solvent removed by distillation. Distillation, however, has some drawbacks. It is expensive due to the energy costs associated with heating the solvent to its boiling point. Furthermore, because taxanes decompose under distillation procedures at atmospheric pressure, vacuum distillation at reduced pressure is required. But even vacuum distillation has unresolved problems. Industrial-sized, low temperature, vacuum distillation is a difficult process due to heat transfer and vacuum problems. Distillation of a miscelle containing taxanes results in decreases in the yield of useful taxanes and increases in the cost of the final product, taxol.

Although distillation has shown many drawbacks, reverse osmosis and ultrafiltration have not been employed as methods for purifying/concentrating taxanes. Taxanes in the miscelle, specifically taxol, have a molecular weight of approximately 850 daltons. Ultrafiltration membranes having over a 1000 daltons nominal molecular weight cutoff, would be expected to pass the taxane material through these membranes showing no concentration. The crudity of the miscelle which contains not only nonaqueous solvent but also a mixture of solutes made the reverse osmosis process highly unlikely to succeed at purifying the desired solute. The reverse osmosis membranes are typically best suited to at least partially purify solutions without mixed solutes.

OBJECTS AND SUMMARY OF THE INVENTION

An object of the present invention is to provide a method for concentrating taxanes in a solution without heating the solvent in the solution to boiling.

Another object of the present invention is to provide a method for processing a solution containing taxanes to concentrate the taxanes therein without decomposition of the taxanes.

Still another object of the present invention is to provide a method of processing a feed liquid to concentrate the desired solute by elimination of undesirable solutes by a process of ultrafiltration.

Yet another object of the present invention is to provide a method of recycling a solvent from a solution.

According to the present invention, there is provided a method of processing a taxane containing feed liquid. This feed liquid is formed as a solution having a solvent constituent and at least one solute constituent. The method of processing this taxane containing feed liquid removes at least one of the solute constituents from the feed liquid by the following steps: providing a semipermeable membrane that separates a first region from a second region; contacting the feed liquid with the first region; and providing pressure sufficient to transport some constituents of the feed liquid from the first region across the membrane to the second region by reverse osmosis. Thus, in the first region a retentate containing at least one solute constituent is formed and in the second region a permeate containing solvent is formed. A further step includes recovery of the respective one of the retentate and the permeate that contains the desired solute constituent.

As indicated earlier, the invention is particularly applicable to the concentration of taxanes in a solution that contains taxanes. The method of processing the solution separates the solute from the solution by the following steps: separating a first region from a second region by a first semipermeable membrane adapted to retain selected solutes and having a pore size of less than 10,001 daltons; placing the feed liquid in the first region; providing pressure sufficient to transport some of the feed liquid from the first region across the first semipermeable membrane to the second region, wherein in the first region there is formed a retentate and in the second region there is formed a permeate. Then, recovering the respective one of the permeate and the retentate which contains the taxanes.

These and other objects of the present invention will become more readily appreciated and understood from a consideration of the following detailed description of the preferred embodiment when taken together with the accompanying drawings.

BRIEF DESCRIPTION OF THE EXEMPLARY EMBODIMENT

The present invention relates to a method for processing a feed liquid in order to remove a solute dissolved or suspended therein. More specifically, this method is particularly useful in the concentration/purification of solutes from a solution containing taxanes wherein undesired residues are present in the solution. This method is described below with respect to the taxane concentration/purification application, and a taxane product prepared by the methodology of this invention is claimed. The present invention concerns application of either reverse osmosis or ultrafiltration processing to taxanes and other compounds. As noted above, the distinction between "reverse osmosis" and "ultrafiltration" is one of the membrane pore size. Where membranes having a "cutoff", i.e., pore size, of less than about 1000 daltons are used to pass compounds having a size less than about 1000 daltons and to retain larger compounds, the process is typically referred to as reverse osmosis. Ultrafiltration membranes have cutoff of greater than about 1000 daltons.

Figure 1:
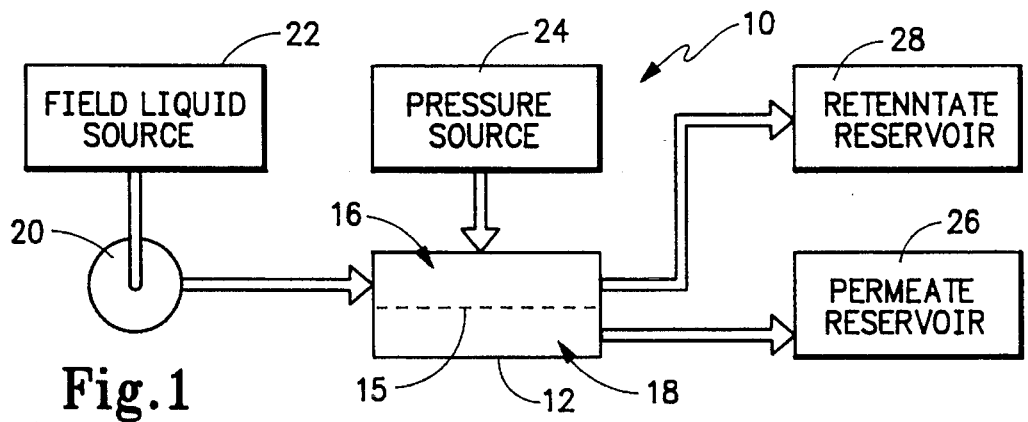
FIG. 1 is a diagrammatic representation of a reverse osmosis/ultrafiltration apparatus as known in the art and as implemented in a first exemplary embodiment of the method according to the present invention.
Figure 2:
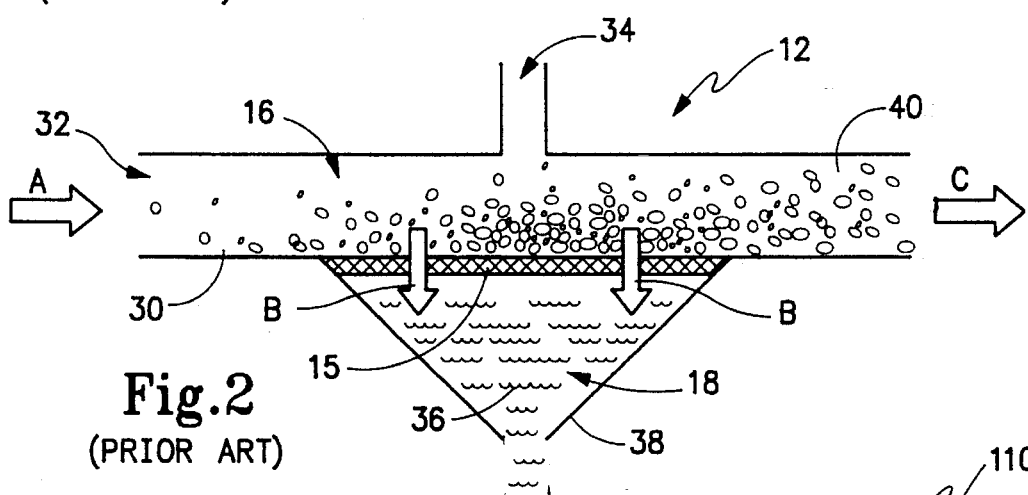
FIG. 2 is a diagrammatic representation of the reverse osmosis/ultrafiltration module shown in FIG. 1.
Figure 3:
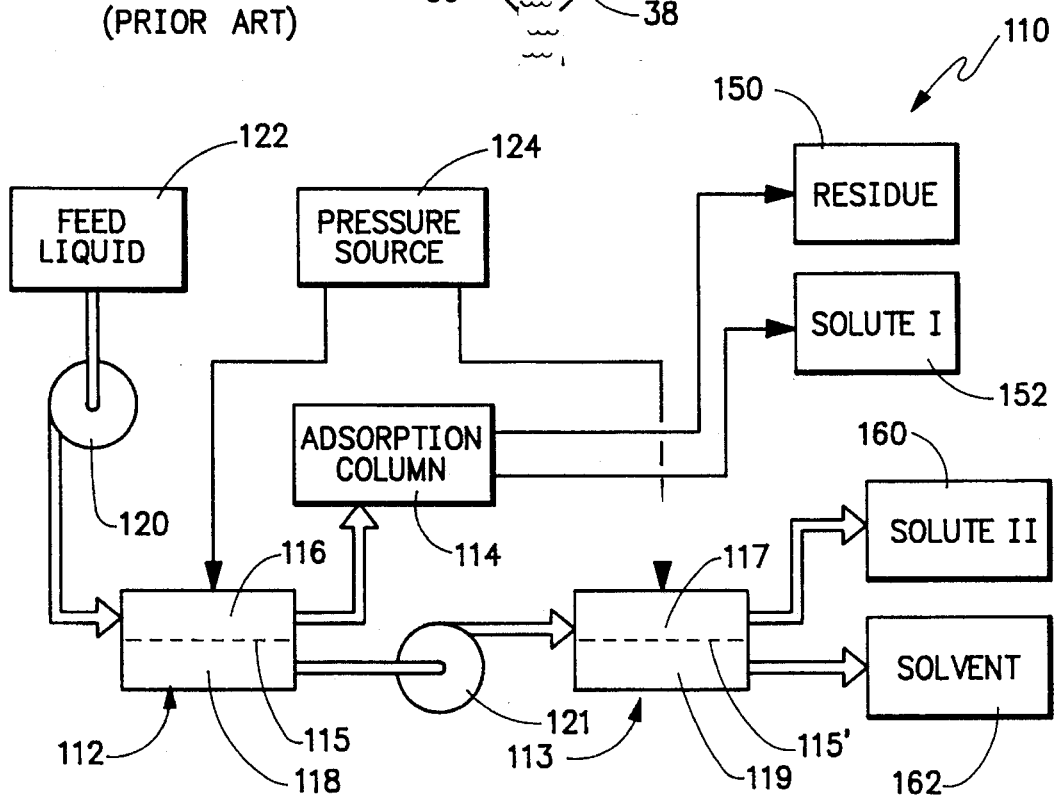
FIG. 3 is a diagrammatic representation of a two-step apparatus as implemented in a second exemplary embodiment of the method according to the present invention.

The reverse osmosis/ultrafiltration process of the present invention utilizes standard equipment known in the art, including the filtration membrane, module, circulation equipment for circulating the feed liquid, pressurization equipment for pressurizing a region on the feed side of the membrane and collection reservoirs for collecting the permeate and the retentate. A diagrammatic view of a first representative reverse osmosis/ultrafiltration apparatus is shown in FIG. 1, and a second representative reverse osmosis/ultrafiltration apparatus is shown in FIG. 3. FIG. 2 depicts a diagrammatic view of a representative membrane module that can be used in either of the apparatus shown in FIGS. 1 and 3.

The apparatus shown in FIG. 1 is typically employed in circumstances where a solute is to be separated from compounds having a molecular weight less than the said solute. Here, a filtration membrane is selected to have a cutoff less than the solute but greater than the other undesired compounds. The desired solute would be retained in the retentate while solvent and the undesired compounds would form the permeate. On the other hand, the apparatus of FIG. 3 might be employed where the desired solute is to be separated from compounds of greater molecular weight. In this case, a first process is used that has a membrane with a cutoff greater than the molecular weight of the desired solute but less than the molecular weight of the undesired compounds. Accordingly, the desired solute and solvent form the permeate while the undesired compounds remain in the retentate. A second process may then be employed to separate the solvent and, perhaps, other undesired compounds, from the desired solute. In this process, a membrane having a cutoff less than the molecular weight of the desired solute causes the solute to be retained as the retentate of the second process while the solvent and smaller compounds pass through the membrane as the second permeate. In either apparatus, representatively shown in FIGS. 1 and 3, it should be understood that the detailed inclusion of manifold, valves, tubing, etc., have been omitted for the sake of simplicity since the "plumbing" of the apparatus is known within the ordinary level of skill in this art.

In FIG. 1, then, a representative apparatus 10 includes a reverse osmosis/ultrafiltration module 12 that is shown to be separate into a first or retentate region 14 and a second or permeate region 16 by a membrane 15. A feed liquid is supplied to reverse osmosis/ultrafiltration module 12 on the retentate region 16 by means of a pump 20 in communication with a feed liquid reservoir or source 22. Pressure is supplied to the retentate region 16 by pressure source 24. This creates a pressure differential across membrane 15 with retentate region 16 being at a greater pressure than permeate region 18. Module 12 operates in a standard manner to separate the feed liquid into a permeate that crosses the membrane 15 and a retentate that does not cross the membrane so that it is "retained" in retentate region 16. In FIG. 1, the permeate is shown to be taken from reverse osmosis/ultrafiltration module 12 and stored in permeate reservoir 26. Retentate from reverse osmosis/ultrafiltration module 12 is stored in reservoir 28.

Modifications of the apparatus 10 are well known so that not all possible variations are depicted in FIG. 1. For example, pressure source 24 could be replaced by a vacuum source connected in communication with permeate region 18 to apply a negative pressure to create the pressure differential across membrane 15. In any event, the type of equipment employed should be elected to accommodate the size of the reverse osmosis/ultrafiltration system and to accommodate the required levels of pressure. Higher pressure tends to shorten the lifespan of the membrane; lower pressure tends to lengthen the lifespan of the membrane. The expense and effort of replacing used membranes should be considered when the pressure source and pressure level are selected. Likewise, there are various membranes that could be employed as membrane 15, and these membranes can have different geometrical configurations, and can be incorporated into different types of modules, as is known in the art.

Generally, there are three geometric shapes of membranes: (1) flat sheet; (2) hollow fiber; and (3) tubular. Flat sheet membranes are configured in sheet-like panels of relatively small thickness. Hollow fiber membranes are formed as continuous annular monofilaments, and tubular membranes are formed as long hollow tubes. Furthermore, the membranes used in reverse osmosis systems are classed chemically as cellulosic or noncellulosic. Cellulosic refers to membranes formed of cellulose acetate, cellulose triacetate and blends of the two. Noncellulosic membranes are formed of a variety of synthetic polymers, for example polysulfone. The actual chemical make-up of the membrane must be taken into account when selecting a membrane since the chemical make-up effects ruggedness and expense. The chemical make-up may also effect the behavior of the membrane in nonaqueous solutions, because these membranes are constructed to filter water solutions and not nonaqueous solvents. Thus, the effect the nonaqueous solvent has on the membrane must be determined.

Membranes are normally mounted in modules that may then be incorporated into a desired system, and the type of module refers to the physical structure used to house the particular membrane to be employed in the reverse osmosis/ultrafiltration process. There are four different modules adapted to contain the different membranes based on the geometry of the membrane. "Spiral wound" modules and "plate and frame" modules are used with flat sheet membranes. "Tubular" modules are used with tubular membranes, and "hollow fiber" modules are used with hollow fiber membranes. In each case, the module supports the membrane and separates the feed and retentate streams from the permeate stream.

With reference to FIG. 2, representative module 12 is shown, in diagrammatic form, as a plate and frame module supporting flat sheet membrane 15. Feed liquid 30 enters module 12 at inlet 32 as is shown by arrow "A". Pressure is supplied at pressure inlet 34 in order to force a permeate 36 through membrane 15, as is shown by arrows "B", and into chamber 38. The resulting retentate 40 may then exit module 12 as is shown by arrow "C". Here, the high pressure feed liquid 30 contains the desired solute 48, and feed liquid 30 contacts the first side 42 of the membrane 15 in the first retentate region 16. In this exemplary embodiment, the feed liquid 30 continuously passes in a tangential flow over the first side 42 of the membrane 5 with a portion of the feed liquid 45 passing through membrane 15 as permeate 36 and the remainder becoming the retentate 40. The fluid velocity of feed liquid 30 in the tangential direction sweeps away much of the retained desired solute 48 which tends to collect at the surface 42 of the membrane 15. The retentate 40 is then recovered and the desired solute may be subjected to further purification.

Due to the removal of a portion of the feed liquid 30, as the permeate 36, the resulting concentration of solute 48 in retentate 40 increases over the original concentration of solute 48 in the original feed liquid 30. Typically, the permeate 36 is discarded or processed to purify and reclaim the solvent. Where it is found that some of the desired solute 48 is passed into the permeate 36, the permeate 36 can be recovered and passed through an adsorption column to recover some of the lost solute 48.

With reference to FIG. 3, as noted above, a two-stage apparatus is disclosed for use when it is desired to remove large and small residues from an intermediately sized solute in a feed liquid. In FIG. 3, a two-stage apparatus 110 is shown wherein a feed liquid is pumped, by means of pump 120 from a feed liquid source 122 and into a first module 112 containing membrane 115. Membrane 115 separates module 112 into a first retentate region 116 and a first permeate region 118. Retentate region 116 is pressurized by virtue of its communication with pressure source 124. The first permeate, containing the smaller solutes including small sized undesired solutes passes through membrane 115 into permeate region 118. It is then pumped, by means of pump 121, into a second module 113. Meanwhile, the retentate remaining in retentate region 116 that now has the larger undesirable solutes removed, may be transported as a concentrate to an absorption column 114. This column may be used to separate the retentate into fractions, at 150, and then into desirable solutes (I) which may be of interest for further processing or which may include some amounts of the smaller desirable solutes that, for one reason or another, did not pass through the membrane. This is represented at 152. Uses of such an absorption column, of course, are well-known in the art.

The permeate is introduced into module 113. Module 113 includes a membrane 115' of smaller pore size than membrane 115 such that it is operative to reject the desired solutes. Filtration membrane 115' separates module 113 into a second retentate region 117 and a second permeate region 119. In this instance, the desired solute (II) does not pass through membrane 115 due to the small pore size of membrane 115 so that solute (II) may be recovered, at 160, as the retentate from module 113. Solvent and smaller sized solutes forming the permeate from module 113 may then be recovered at 162. As before, these solvents and solutes may be further processed to purify the solvents or solutes, as desired.

The present invention departs from standard reverse osmosis/ultrafiltration methodology both in its application to the recovery of taxanes from biomass. As is known, taxanes are present in plant material, especially the taxus species (Taxaceae) such as the Pacific Yew tree, *Taxus brevifolia*. Taxanes extracted from this plant material which are of particular interest in the medical field are taxol, and other taxanes from which taxol can be synthesized, such as Baccatin III, 10-deacetyltaxol, cephalomannine, 10-deacetyl Baccatin III and the like.

The present invention applies reverse osmosis/ultrafiltration techniques to solvent systems used to extract taxanes from biomass in a manner not to be expected and surprisingly resulting in the efficient recovery of the taxanes. The biomass in the preferred embodiment is the bark or leaves and twigs from *Taxus brevifolia*.

Typical solvents used to extract taxanes from the taxus biomass are alcohols such as methanol, ethanol, or mixtures of organic solvents such as methanol and methylene chloride. These organic solvents are typically contacted with a wet biomass, and a solution is extracted from the biomass by the solvent. This solution is the miscelle which is a crude mixture of compounds. The miscelle contains the solvent, and the desired solute, which in the preferred embodiment is a taxane compound and other compounds that may be both larger and smaller molecular weight than the molecular weight of the taxanes. This miscelle may therefore define the feed liquid for the reverse osmosis/ultrafiltration processing.

The resulting miscelle in the preferred embodiment of this invention is accordingly a nonaqueous solution formed of a nonaqueous solvent and taxanes as at least one of the solutes. It has also been found that reverse osmosis/ultrafiltration membranes behave unexpectantly when the feed liquid is nonaqueous. In the process of developing the present invention, it was discovered that a nonaqueous solvent present in the feed liquid affects the expected permeability of the membrane, and about half of the tested membranes exhibited uncharacteristic behavior in the presence of the feed liquid. This may be because reverse osmosis membranes often are hydrophilic in their nature. Nonaqueous solvents tend to change the amount of hydration and, thus, the permeability of the membrane's surface. Therefore, some membranes that are adapted to pass solute material having a molecular weight of less than 1000 daltons in an aqueous solution will retain the majority of solute material having a molecular weight of 850 daltons if the solution is crude miscelle.

For example, if the desired solute is taxol or another taxane then the molecular weight of the desired solute will be 850 daltons. Thus, a 1000 nominal molecular weight cutoff membrane would be expected to pass the solute into the permeate and a 500 nominal molecular weight cutoff membrane would be expected to retain the solute. However, these expected results are not necessarily achieved. Some membranes having nominal molecular weight cutoff of 1000 daltons passed 90% of the taxanes, some membranes having nominal molecular weight cutoff of 1000 daltons retained approximately 90%. A 10,000 nominal molecular weight cutoff membrane passed only 90% of the taxanes retaining 10% while a 500 nominal molecular weight cutoff membrane passed 4% of the taxane material. It appears that at least three factors may be effecting the permeability of the membranes, the chemical composite of the membrane, the solvent and solute used in the feed liquid and the manufacturer's quality control standards.

Before reviewing the examples of reverse osmosis/ultrafiltration discussed below, it should be understood that, in the present invention, a flat sheet, cellulose acetate membrane from Millipore, Inc. was employed in a Millipore spiral wound ultrafiltration cartridge or a Helicon 50 sq. ft. spiral wound cartridge to separate the taxanes. However, any of the modules, shapes of membranes and membrane types can be employed in the present invention. The feed liquid was a solution containing an alcohol solvent and the desired solute, taxane. If the alcohol solvent was passed through a biomass such as *Taxus brevifolia* and then stored, the resultant miscelle may have residue solutes of greater than 5000 daltons molecular weight. Thus, a 5000 nominal molecular weight cutoff membrane may be used to reject the undesirable solutes and residue into the retentate.

The use of a 5000 nominal molecular weight cutoff membrane is particularly useful if the feed liquid that contains taxanes has either been heated or has been stored for an extended period of time after extraction from the biomass. Heated or stored feed liquids tend to have large molecular weight residue which can be removed with the 5000 nominal molecular weight cutoff membrane. If the feed liquid has not been subjected to adverse conditions then a 1000 nominal molecular weight cutoff membrane that behaves characteristically (i.e., passes solutes smaller than 1000 daltons) should typically be employed. It should also be understood by those with ordinary skill in this art that feed liquids containing only small amounts of undesired solutes of a size larger than the size of the desired solute would not need to be processed through the solute permeable membrane and could just be passed through a membrane that would reject the desired solutes and pass a majority of the solvent into the permeate.

In certain instances, therefore only a one step process wherein the feed liquid containing taxane and solvent is processed through a 1000 nominal molecular weight cutoff reverse osmosis membrane can be employed, if this membrane effectively retains most of the taxane in the retentate. (Although 1000 nominal molecular weight cutoffs membranes would be expected to pass the 850 daltons taxanes). In the two-stage process of the present invention, it is preferred that the first membrane 115 passes most of the taxanes into the first permeate. The second membrane 115' is a membrane that rejects the 850 dalton taxane solute in nonaqueous solution. Knowing the nominal molecular weight cutoff pore size of a specific membrane is not sufficient, however, since the crude miscelle that makes up the first solutions affect different membranes differently, as will be seen in the examples set forth below.

The following non-limiting examples, then, provide data on the enrichment of taxanes and specifically taxol resulting from a two membrane reverse osmosis method in accordance with the present invention, of the type diagrammed in FIG. 3. All scientific and technical terms have the meaning as understood by one with ordinary skill in the art. In each of the three following examples, a selected quantity of miscelle, formed of a methanolic extract of *Taxus brevifolia* bark, was analyzed to determine the taxol purity of the solution.

| | |
|---|---|
| Taxol purity of feed liquid | .22% taxol |
| Reaction temperature | room temperature |
| PSI in high pressure filter housing | 60–80 psi |
| Diameter of membranes | 1 inch |
| First membrane | 1000 nominal molecular weight cutoff Spectrum (Type C) |
| Second membrane | 500 nominal molecular weight cutoff Micro Filtration Systems (MFS) |
| Chemical composition | cellulose of first membrane acetate |
| Chemical composition of second membrane | polyionic |

A selected quantity of feed liquid was subjected to reverse osmosis under 60–80 psi pressure drop through the first membrane. The permeate and retentate was collected and assessed for the percent taxol present and the purity of the taxol. The 1000 nominal molecular weight cutoff Spectrum membrane had the following results:

| A. First Membrane | | |
|---|---|---|
| | Retentate | Permeate |
| Distribution of taxol | 0–5% | 85–90% |
| Distribution of residue | 32% | 63% |
| Purity of taxol | .02% | .29% |
| Enrichment of taxol compared to feed liquid | | 1.32× |

The 1000 nominal molecular weight cutoff membrane passed taxol material which is approximately 850 daltons. Approximately 5% of the taxol was lost during this step. The permeate liquid which was recovered contained 1.32 times the amount of taxol per residue (weight per unit volume) when compared with the taxol found in the feed liquid per residue. This permeate was then passed through a second membrane as described below.

| B. Second Membrane | | |
|---|---|---|
| | Retentate | Permeate |
| Purity of taxol taxol | .32% | .53% |
| Enrichment of taxol compared to feed liquid | | 1.45× |

The permeate was subjected to reverse osmosis under a 60–80 psi pressure drop through the membrane. The 500 nominal molecular weight cutoff membrane retained most of the taxol with only 5–10% taxol being lost in the permeate. The permeate had a high percentage of taxol, 0.53%, however, the actual amount of taxol in the permeate was extremely small and the bulk of the taxol was in the retentate. The taxol in the retentate of the second membrane had an increased purity of 1.45 times when compared to the original feed liquid.

| | |
|---|---|
| Taxol purity of feed liquid | .25% taxol |
| Reaction temperature | room temperature |
| PSI in high pressure filter housing | 60–80 psi |
| Diameter of membranes | 1 inch |
| First membrane | 1000 nominal molecular weight cutoffs Spectrum (Type C) |
| Second membrane | 500 nominal molecular weight cutoffs Spectrum (Type C) |
| Chemical composition of first membrane | cellulose acetate |
| Chemical composition of second membrane | cellulose acetate |

A selected quantity of feed liquid was subjected to reverse osmosis under a 60–80 psi pressure drop through the first membrane. The permeate and retentate were collected and assessed for percent taxol, percentage of residue, and percent purity of taxol. The 1000 nominal molecular weight cutoff Spectrum membrane had the following results:

| A. First Membrane | | |
|---|---|---|
| | Retentate | Permeate |
| Distribution of taxol | 1% | 99% |
| Distribution of residue | 32% | 68% |
| Purity of taxol | .02% | .23% |
| Enrichment of taxol compared to feed liquid | | 1.24× |

As was expected the majority of the taxol was passed through the 1000 nominal molecular weight cutoff Spectrum membrane into the retentate. The first pass through this membrane enriched the taxol content of the permeate 1.24 times the taxol content of the feed liquid. This permeate was then passed through a second membrane under pressure as described.

| B. Second Membrane | | |
|---|---|---|
| | Retentate | Permeate |
| Purity of taxol taxol | 31% | .34% |
| Enrichment of taxol compared to feed liquid | | 1.36× |

The permeate was subjected to reverse osmosis under a 60–80 psi pressure drop through the membrane. Unexpectedly, the 500 nominal molecular weight cutoff Spectrum membrane did not retain the taxol. In fact, 75% of the taxol which has a 850 daltons molecular weight was passed into the permeate. In spite of this loss of taxol into the permeate, the retentate had a taxol enrichment that was 1.36 times that of the feed liquid. Of course, the permeate could be further passed through an adsorption column or alternatively, filtered through smaller nominal molecular weight cutoff membranes to attempt to recover a portion of the lost taxol. Filtering the permeate through a 500 nominal molecular weight cutoff membrane from Micro Filtering Systems (MFS) as was done in Example I should recover most of the lost taxol. The difference between the performance of the Spectrum 500 nominal molecular weight cutoff membrane and the MFS 500 nominal molecular weight cutoff membrane was probably a result of the difference in chemical make-up of the two membranes, the use of a nonaqueous solvent and the difference between quality control standards of the individual companies that made the membranes.

| | |
|---|---|
| Taxol purity of feed liquid | .22% taxol |
| Reaction temperature | room temperature |
| PSI in high pressure filter housing | 60–80 psi |
| Diameter of membranes | 1 inch |
| First membrane | 1000 nominal molecular weight cutoffs Spectrum (Type C) |
| Second membrane | 1000 nominal molecular weight cutoffs Koch |
| Chemical composition of first membrane | cellulose acetate |
| Chemical composition of second membrane | polysulfone |

A selected quantity of nonaqueous feed liquid was subjected to reverse osmosis under 60–80 psi pressure drop through the first membrane. The permeate and retentate were collected and assessed for the percentage of taxol, residue, and purity of taxol. The 1000 nominal molecular weight cutoff Spectrum membrane had the following results:

| A. First Membrane | | |
|---|---|---|
| | Retentate | Permeate |
| Distribution of taxol | 9% | 91% |
| Distribution of residue | 34% | 66% |
| Purity of taxol | .06% | .30% |
| Enrichment of taxol compared | | 1.40× |

| A. First Membrane | | |
|---|---|---|
| | Retentate | Permeate |
| to feed liquid | | |

Because the first two experiments evidenced a strong difference between two membranes which were expected to behave similarly a comparison of two 1000 nominal molecular weight cutoff membranes having different manufacturers and different composition was performed. The resultant enrichment of the taxol was highly surprising. Of course, two 1000 nominal molecular weight cutoff membranes would be expected to pass 100% of the taxol into the permeate resulting in little to no increase in the concentration of taxol in the resultant fluid. In this experiment, the 1000 nominal molecular weight cutoff Spectrum membrane behaved characteristically and passed all but 9% of the taxol when subjected to reverse osmosis under a 60–80 psi drop through the membrane. The retentate retained 33% of the residue; thus, purifying the taxol and concentrating the taxol in the permeate. In fact, the permeate contained 1.4 times the purity of taxol compared with the feed liquid. The permeate was then passed through a second membrane.

| B. Second Membrane | | |
|---|---|---|
| | Retentate | Permeate |
| Purity of taxol taxol | 80% | .05% |
| Enrichment of taxol compared to feed liquid | | 3.6× |

The permeate was subjected to reverse osmosis under a 60–80 psi pressure drop through the second membrane. The 1000 nominal molecular weight cutoff Koch membrane did not react as would be anticipated. The Koch membrane retained all but 10% of the taxol that was in the permeate from the first membrane. Furthermore, 44% of the residue was passed through the membrane into the permeate. Thus, the retentate was a highly concentrated and purified taxol solution. The unanticipated behavior of the Koch membrane resulted in a substantial enrichment of the taxol in the resultant fluid. There was 3.6 times the amount of taxol per residue weight in the resultant fluid when compared with the amount of taxol per residue weight in the original feed liquid.

The use of a reverse osmosis or an ultrafiltration process with crude miscelle solutions and specifically with taxanes provides a number of advantages. The reverse osmosis or ultrafiltration process increases the purity of the taxol in the resultant fluid at least up to 3½ times the purity of the taxanes in the feed liquid. This purification and concentration is achieved without heating the solvent and thus, decomposing the desired material or causing polymerization of other material for example tannins which would have to be removed in a later purification step. Taxanes purified by the reverse osmosis or ultrafiltration method are better "behaved" in subsequent processing steps primarily because the effects of heating the process are not evidenced.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

I claim:

1. A method of processing a feed liquid in the form of an extraction solution that is an extraction product of a biomass wherein the extraction solution contains taxane solutes as at least one solute constituent and having a solvent constituent to remove at least one solute constituent from the feed liquid, comprising the steps of:

providing a semipermeable membrane that separates a first region from a second region;

placing said feed liquid containing said taxane solutes in said first region such that said feed liquid contacts said membrane; and providing pressure sufficient to transport some constituents of the feed liquid from said first region across said membrane to said second region by reverse osmosis wherein a retentate containing at least one solute constituent is formed in said first region and a permeate containing a portion of the solvent constituent is formed in said second region.

2. A solution containing taxane solutes produced by the method according to claim 1.

3. A solution according to claim 2 wherein said retentate contains said taxane solutes.

4. A solution according to claim 2 wherein said permeate contains said taxane solutes.

5. A method according to claim 1 wherein said solvent constituent is an alcohol.

6. A method according to claim 5 wherein said alcohol is methanol.

7. A method according to claim 5 wherein said alcohol is ethanol.

8. A method according to claim 1 wherein said solvent constituent is an ether.

9. A method according to claim 8 wherein said ether is methyltertiarybutylether.

10. A method according to claim 1 wherein said membrane is retained in a module.

11. A method according to claim 1 wherein said membrane is cellulosic.

12. A method according to claim 1 wherein said membrane is noncellulosic.

13. A method according to claim 1 wherein said membrane is selected from a group consisting of hollow fiber, flat sheet and tubular membranes.

14. A method according to claim 10 wherein said module is selected from a group consisting of plate and frame, spiral wound, tubular, and hollow fiber modules.

15. A method according to claim 1 wherein said membrane has a molecular weight cutoff less than 10,001 daltons.

16. A method of processing a feed liquid in the form of an extraction solution that is an extraction product of a biomass wherein the extraction solution contains a taxane solute as at least one constituent and having a solvent constituent, comprising the steps of:

forming a feed liquid by exposing plant material containing taxanes to a solvent adapted to remove said taxanes from said plant material, said feed liquid thereby forming said extraction solution that contains the taxane solutes and residue;

separating a first region from a second region by a first semipermeable membrane adapted to retain selected solutes and having a pore size of less than 10001 daltons;

placing the extraction solution in the first region;

providing pressure sufficient to transport some of the extraction solution from said first region across said first semipermeable membrane to said second region wherein in said first region is formed a retentate and in said second region is formed a permeate; and recovering the respective one of said permeate and said retentate which contains said taxanes which were in said feed liquid.

17. A method according to claim 16 including the step of recovering solvent from at least one of said permeate and said retentate.

18. A method according to claim 16 wherein after recovering the respective one of said permeate and said retentate which contain the taxane, said respective one is transported across a second membrane wherein there is formed a second retentate and a second permeate, and said second retentate contains said taxane.

19. A method according to claim 18 including the step of recovering the respective one of said second permeate and said second retentate which contains said taxane.

20. A method according to claim 18 wherein said first membrane has a greater pore size than said second membrane.

21. A method according to claim 18 wherein said first membrane has the same pore size as said second membrane.

22. A method according to claim 16 including the step of purifying the respective one of said permeate and said retentate which contains said taxane.

23. A purified taxane product produced by the method according to claim 22.

24. A method of processing a feed liquid that contains desired taxane solutes, undesired solutes that have molecular sizes larger and smaller than the desired taxane solutes and a solvent as constituents of said feed liquid in order to concentrate the desired taxane solutes, comprising the steps of:

(a) separating a first region from a second region by a first semipermeable membrane of a first pore size and composition which transports a majority of the desired taxane solutes therethrough yet retains at least some of said undesired solutes;

(b) placing the feed liquid in the first region;

(c) providing pressure sufficient to transport some of the feed liquid from said first region across said first semipermeable membrane to said second region as a first permeate containing a majority of desired taxanes and thereby form a first retentate in said first region;

(d) separating a third region from a fourth region by a second semipermeable membrane of a second pore size and composition different from said first semipermeable membrane which second pore size and composition retains a majority of the desired taxane solutes present in said first permeate yet transports at least some of said undesired solutes therethrough;

(e) placing the first permeate in the third region;

(f) providing pressure sufficient to transport at least some of the first permeate from said third region across said second semipermeable membrane to said fourth region as a second permeate thereby to form a second retentate in said third region; and (g) recovering the desired taxane solutes from said second retentate.

* * * * *